United States Patent
Gosiengfiao et al.

(10) Patent No.: US 7,713,259 B2
(45) Date of Patent: May 11, 2010

(54) GUIDING CATHETER SHAFT WITH IMPROVED RADIOPACITY ON THE WIRE BRAID

(75) Inventors: Brandon Gosiengfiao, Temecula, CA (US); Jonathan M. Howland, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/049,544

(22) Filed: Mar. 17, 2008

(65) Prior Publication Data
US 2008/0161776 A1    Jul. 3, 2008

Related U.S. Application Data

(63) Continuation of application No. 10/385,987, filed on Mar. 11, 2003, now Pat. No. 7,354,428.

(51) Int. Cl.
*A61M 25/098* (2006.01)

(52) U.S. Cl. ............... 604/529; 604/524; 604/527; 604/528

(58) Field of Classification Search .......... 604/523–529
See application file for complete search history.

(56) References Cited

U.S. PATENT DOCUMENTS

| 4,657,024 | A | * | 4/1987 | Coneys | 600/435 |
|---|---|---|---|---|---|
| 5,451,209 | A | | 9/1995 | Ainsworth et al. | |
| 5,527,325 | A | | 6/1996 | Conley et al. | |
| 5,906,605 | A | | 5/1999 | Coxum | |
| 7,112,298 | B2 | | 9/2006 | Kampa et al. | |
| 7,354,430 | B2 | * | 4/2008 | Pepin | 604/525 |

* cited by examiner

*Primary Examiner*—Kevin C Sirmons
*Assistant Examiner*—Bhisma Mehta
(74) *Attorney, Agent, or Firm*—Fulwider Patton LLP

(57) ABSTRACT

An intracorporeal catheter, such as a guiding catheter, employed for intraluminal procedures is disclosed. The catheter generally has an elongated catheter shaft including a polymeric inner layer and a non-radiopaque outer polymeric layer, along with a radiopaque reinforcing structure disposed between the inner and outer layers. In one embodiment, the reinforcing layer consists of multiple drawn filled tubes braided or wound together. The drawn filled tubes may have a stainless steel outer jacket clad over a radiopaque inner core, or the drawn filled tubes may have a radiopaque outer jacket clad over a stainless steel core. In another embodiment, the reinforcing layer may consist of multiple wires containing radiopaque alloys braided or wound together, wherein at least two of the wires consist of different radiopaque alloys. The strands of the reinforcing structure may have a circular or a rectangular transverse cross-sectional shape.

9 Claims, 2 Drawing Sheets

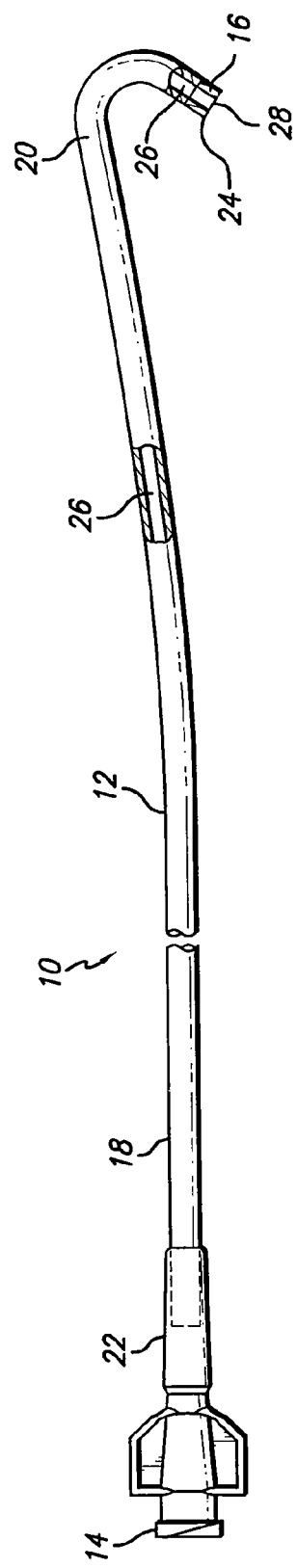
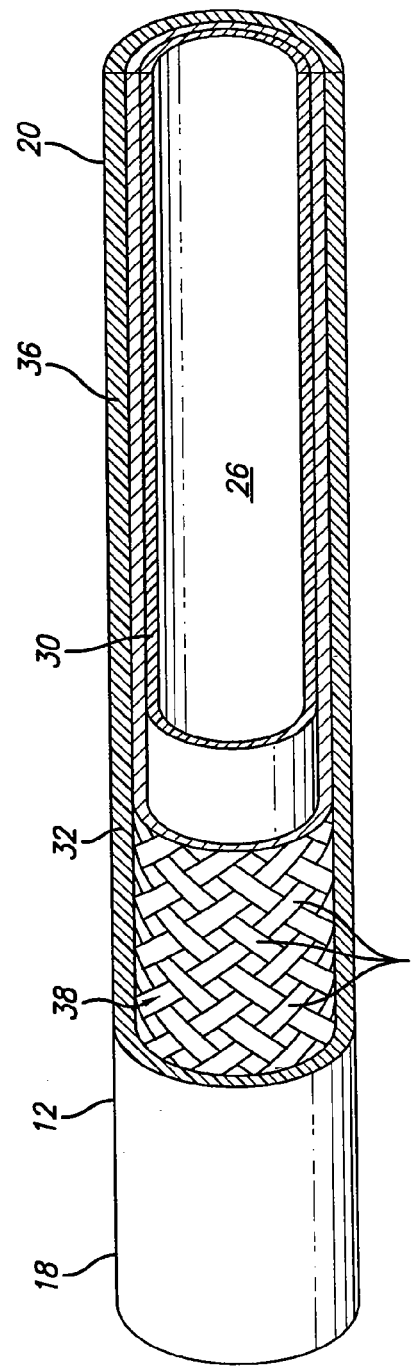

GUIDING CATHETER SHAFT WITH IMPROVED RADIOPACITY ON THE WIRE BRAID

CROSS-REFERENCE TO RELATED APPLICATIONS

This is a continuation of U.S. Ser. No. 10/385,987, filed Mar. 11, 2003, now U.S. Pat. No. 7,354,428, the contents of which are hereby incorporated by reference.

BACKGROUND OF THE INVENTION

The invention relates to the field of intraluminal catheters, and particularly to guiding catheters suitable for intravascular procedures such as angioplasty, stent deployment, pacing lead deployment and the like.

In percutaneous transluminal coronary angioplasty (PTCA) procedures a guiding catheter having a shaped distal section is percutaneously introduced into the patient's vasculature and then advanced through the patient's vasculature until the shaped distal section of the guiding catheter is adjacent to the ostium of a desired coronary artery. The proximal end of the guiding catheter, which extends out of the patient, is torqued to rotate the shaped distal section and, as the distal section rotates, it is guided into desired coronary ostium. The distal section of the guiding catheter is shaped so as to engage a surface of the ascending aorta and thereby seat the distal end of the guiding catheter in the desired coronary ostium and to hold the catheter in that position during the procedures when other intravascular devices such a guide wires and balloon catheters are being advanced through the inner lumen of the guiding catheter.

In the typical PTCA or stent delivery procedures, the balloon catheter with a guide wire disposed within an inner lumen of the balloon catheter is advanced within the inner lumen of the guiding catheter which has been appropriately positioned with its distal tip seated within the desired coronary ostium. The guide wire is first advanced out of the distal end of the guiding catheter into the patient's coronary artery until the distal end of the guide wire crosses a lesion to be dilated or an arterial location where a stent is to be deployed. A balloon catheter is advanced into the patient's coronary anatomy over the previously introduced guide wire until the balloon on the distal portion of the balloon catheter is properly positioned across the lesion. Once properly positioned, the balloon is inflated with inflation fluid one or more times to a predetermined size so that in the case of the PTCA procedure, the stenosis is compressed against the arterial wall and the wall expanded to open up the vascular passageway. In the case of stent deployment, the balloon is inflated to plastically expand the stent within the stenotic region where it remains in the expanded condition. Generally, the inflated diameter of the balloon is approximately the same diameter as the native diameter of the body lumen being dilated so as to complete the dilatation or stent deployment but not overexpand the artery wall. After the balloon is finally deflated, blood flow resumes through the dilated artery and the dilatation catheter and the guide wire can be removed therefrom. Generally, the stent deployment may be accomplished simultaneously with or after a PTCA procedure has been performed at the stenotic site.

In addition to their use in PTCA and stent delivery procedures, guiding catheters are used to advance a variety of electrophysiology-type catheters and other therapeutic and diagnostic devices into the coronary arteries, the coronary sinus, the heart chambers, neurological and other intracorporeal locations for sensing, pacing, ablation and other procedures. For example, one particularly attractive procedure for treating patients with congestive heart failure (CHF) involves introduction of a pacing lead into the patient's coronary sinus and advancing the lead through the patient's great coronary vein and a branch of the great coronary vein until the distal end of the pacing lead is disposed at a location which allows the electrical impulses from the pacing lead to pace the left ventricle of the patient's heart. A second pacing lead may be disposed within the patient's right ventricle or a cardiac vein draining the patient's right ventricle and both the left and right ventricle may then be paced by the pacing leads, resulting in greater pumping efficiencies and greater blood flow out of the heart which minimizes the effects of CHF.

Current construction of many commercially available guiding catheters include an elongated shaft of a polymeric tubular member with reinforcing strands (usually metallic, high strength polymers or combinations thereof) within the wall of the tubular member. The strands are usually braided or wound into a reinforcing structure. The desired shape in the distal section of the catheter, which facilitates its deployment at the desired intracorporeal location such as the coronary sinus, is typically formed by holding the distal section in the desired shape and heat setting the polymeric material in the distal section of the catheter wall to maintain the desired shape. There is usually some spring-back after the heat formation due to the reinforcing braid, but this is usually compensated for in the shape the catheter is held in during the heat setting.

The current guiding catheter shafts also have outer polymer jackets with radiopaque fillers embedded in the resin. Clinical requirements for utilizing guiding catheters to advance catheters and other intravascular devices have resulted in a need for increased transverse dimensions of the inner lumens of guiding catheters to accommodate a greater variety of large intracorporeal devices with little or no increase in the outer transverse dimensions of the guiding catheter to present a low profile which facilitates advancement within the patient's body lumens and openings. These catheter design changes have required a reduction in the wall thickness which in turn requires the outer polymer jacket to be thinner on the wall. The combination of the thin wall polymer jacket along with large amounts of radiopaque fillers such as bismuth, bismuth oxychloride and tungsten may cause the outer polymer jacket to split or break during torsional movement. When the radiopaque filler ratio exceeds the polymer resin ratio, the outer polymer jacket has lower ductility which causes the splits and tears. Reduction of wall thickness also translates into a reduction in the ratio of polymer to stranded reinforcement and/or a reduction in strand thickness. These factors result in a catheter shaft which may not have the requisite mechanical properties such as torqueability or kink-resistance.

What has been needed is a catheter design which would allow for continued thinning of the catheter wall for increased lumen size in conjunction with low outer profiles, improved radiopacity, while providing the mechanical and physical properties that are clinically desirable for such products, and preventing tearing, cracking, bend kinks and torsional breaks in the outer jacket of the catheter. The present invention satisfies these and other needs.

SUMMARY OF THE INVENTION

The present invention is generally directed to a thin walled intraluminal catheter, such as a guiding catheter, accessing coronary arteries or cardiac veins which have relatively large internal luminal dimensions with the catheter wall having clinically desirable structural properties. In one embodiment, the present invention catheter features a reinforcing layer with improved radiopacity.

One intraluminal catheter embodying features of the invention has an elongated shaft with a preshaped or shapeable distal shaft section to facilitate placement of the distal tip of the catheter into a patient's blood vessel or body lumen. The shaft has a multistrand reinforcing structure or layer that is radiopaque, preferably within the wall of the shaft, which may be braided or wound. The proximal shaft section of the catheter has a polymeric outer layer containing no radiopaque fillers, a polymeric inner layer with the braided or wound multistrand reinforcing structure disposed between the inner and outer layers. The inner layer is formed of a sufficiently lubricious material such as, but not limited to, polyimide, polyamide, polyetheretherketone, expanded ultra high molecular weight polyethylene, or a fluoropolymer such as Teflon®.

The polymeric inner layer and the multistrand reinforcing structure extend through the proximal shaft section and most of the distal shaft section, but usually terminate proximal to the distal end of the catheter shaft to provide atraumatic characteristics to the distal tip. Further, the distal end of the catheter shaft is typically provided with an atraumatic distal tip. The outer layer along at least a distal part of the distal shaft section could be formed of a polymeric material such as polyimide, or a more flexible material on the proximal shaft section and may be a polyamide elastomer, e.g., a polyether block amide such as PEBAX alone or blended with nylon or PEBAX materials with other durometers. Other suitable polymeric materials for the distal outer layer include polyurethanes. A variety of other thermoplastic and thermoelastic polymers, copolymers and blends may also be employed.

The outer polymer jacket or jackets may then be provided on the exterior of the reinforcing structure by suitable means such as heat shrinking, extruding or dip forming a polymeric layer of the desired composition onto the surface of the reinforcing structure. The outer polymer jacket contains no radiopaque fillers to provide a thin wall and to avoid splitting, cracking, or tearing during torsional movement. A removable mandrel may be provided within the inner lumen defined by the inner lining during the manufacturing process to shape the catheter into its desired configuration while it is being formed.

One embodiment of the catheter shaft includes a polymeric tube which forms the inner lining for the catheter shaft with a reinforcing structure having multiple strands (e.g. 4 to 32 strands, typically 12, 16, or 24 strands) of a material in the form of a drawn filled tube having an outer jacket clad over an inner core. The outer jacket may include stainless steel, or other material with similar characteristics, and the inner core preferably includes a radiopaque material. The radiopaque material may include platinum, gold, silver, tantalum, or other radiopaque element. It is possible for the drawn filled tube to have a flat or round cross-section, and to be braided or wound about the inner tubular member which forms the inner layer.

In another embodiment, the outer jacket of the drawn filled tube may be a radiopaque material and the inner core may include stainless steel or other material with similar characteristics. A sufficient number of the drawn filled tube strands are provided to reach the desired radiopacity of the guiding catheter. By using drawn filled tube wires that have a radiopaque core, the need for radiopaque filler in the outer jacket is eliminated.

In yet another embodiment, the reinforcing structure may be formed by using multiple spools of wires consisting of different radiopaque alloys having similar mechanical properties to stainless steel to provide adequate torque transmission and stiffness. It is also contemplated that a spool containing stainless steel or similar material may also be used in this embodiment. In one embodiment, at least two of the spools are different radiopaque alloys, such as MP35N, Conichrome, and Haynes 242. Other alloys may be used that have radiopaque properties and equivalent stainless steel properties. As a result of using different spools of wires, the sum of the radiopaque alloys used to form the reinforcing layer will determine the amount of radiopacity detected under fluoroscopy.

In all of the mentioned embodiments for the radiopaque reinforcing layer, the combination of the number of picks, pitches and wire geometry, such as flat or round, will enhance the visualization of the guiding catheter shaft under fluoroscopy while preserving the torque and stiffness properties. These embodiments will also allow the inside diameter of the catheter to be larger while preserving the outside diameter of the catheter, and will prevent the outer layer from cracking or tearing during torsional movement.

These and other advantages of the invention will become more apparent from the following detailed description of the invention and the accompanying exemplary drawings.

BRIEF DESCRIPTION OF THE DRAWINGS

FIG. 1 is a side elevational view of a guiding catheter embodying features of the invention.

FIG. 2 is a partial cutaway perspective view of the elongated shaft of the catheter shown in FIG. 1 having a reinforcing structure formed of flat wires.

DETAILED DESCRIPTION OF THE PREFERRED EMBODIMENTS

Figure 2A:
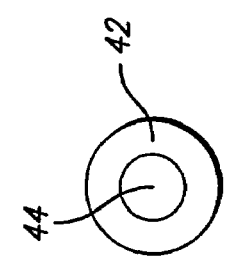
FIG. 2A is a cross-sectional view of a flat wire as shown in FIG. 2.

FIG. 1 illustrates an embodiment of a catheter 10 generally including an elongated catheter shaft 12 with a proximal end 14 and a distal end 16. The elongated catheter shaft 12 also has a proximal shaft section 18 and a distal shaft section 20 which is at least partially shaped, an adapter 22 mounted on the proximal end 14, an atraumatic distal tip 24, and an inner lumen 26 which extends within the catheter shaft 12 from the proximal end 14 thereof to a port 28 located in the distal end 16 of the shaft. The adapter 22 on the proximal end 14 of the catheter may be formed of conventional polymeric materials such as polycarbonate.

As shown in greater detail in FIG. 2, the proximal shaft section 18 of the elongated catheter shaft 12 has an inner polymeric layer 30 and an outer polymeric layer 32. The distal shaft section 20 has inner polymeric layer 30 and an outer polymeric layer 36. A reinforcing structure or layer 38 formed of multiple strands 40 is disposed between the inner and outer polymeric layers 30, 32, and 36, respectively.

The outer layer 32 of the proximal shaft section 18 is preferably formed of polyimide, and the polyimide layer may extend over a length of about 40 to 100% of the total length of the catheter. The thickness of the outer layer 32 formed of polyimide can vary depending on the degree of stiffness required, and is usually between about 0.0005 to about 0.008 inch (0.013-0.205 mm). Depending upon wall thickness requirements, the proximal portion of the outer layer 32 may be a film-dipped thermoset polyimide. Polyimide has several desired characteristics that are useful for a catheter, including a very high stiffness, kink resistance, tight tolerances, and good composite characteristics. Moreover, the stiffness of the polyimide increases the pushability of a thin walled catheter design, and the tight tolerances allow the polyimide coating process to hold about five times as tight of outer diameter tolerances than can be achieved by extruding.

The outer layer 36 of the distal shaft section 20 may not be coated with polyimide, because it is desired to have a more flexible distal end. To attain this flexible quality, the outer layer 36 of the distal shaft section 20 may be formed preferably with a polyamide elastomer, e.g., a polyether block amide such as PEBAX alone or blended with nylon or PEBAX materials with other durometers. The presently suitable polymeric materials are various durometers of PEBAX or nylon. Other suitable polymeric materials for the distal outer layer 36 include polyurethanes. A variety of other thermoplastic and thermoelastic polymers, copolymers and blends may also be employed.

In the present invention, the outer layer 32 alone, or the outer layers 32 and 36 optionally do not contain any radiopaque fillers such as bismuth, bismuth oxychloride, or tungsten. This allows the outer layer to have a thin wall without an increased risk of splits and tears along the outer layer during torsional movements. The guiding catheter of the present invention can still be seen under fluoroscopy, because the reinforcing layer includes radiopaque material, which will be discussed in more detail below.

The polymer layer 30 of the shaft 12 is optionally formed of lubricious material or has a lubricious inner surface. In one embodiment, the lubricious material is a fluoropolymer such as Teflon®, although polyimide, polyamide, expanded ultra high molecular weight polyethylene (eUHMWPE), polyetheretherketone (PEEK) and other tubing may be utilized as well.

In one embodiment of the catheter shaft, the reinforcing layer 38 has multiple strands (e.g. 4 to 32 strands, typically 12, 16 or 24 strands) of a material in the form of a drawn filled tube (DFT) having an outer jacket clad over an inner core. The multiple strands 40 as shown in FIG. 2, are flat drawn filled tube wires, and are braided. However, the drawn filled tube wires can also be wound around the inner layer 30 to form the reinforcing structure. A cross-sectional view of the flat drawn filled tube wires is shown in FIG. 2A, which depicts the outer jacket 42 surrounding the inner core 44. In this embodiment, the outer jacket 42 may include stainless steel, or other material with similar characteristics, and the inner core 44 may include a radiopaque material. The radiopaque material may include platinum, gold, silver, tantalum, or their alloys or other radiopaque elements at levels of about 5%-25% by cross-sectional area of the drawn filled tube.

Figure 3A:
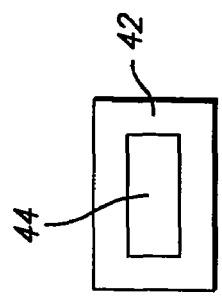
FIG. 3A is a cross-sectional view of a round wire as shown in FIG. 3.
Figure 3:
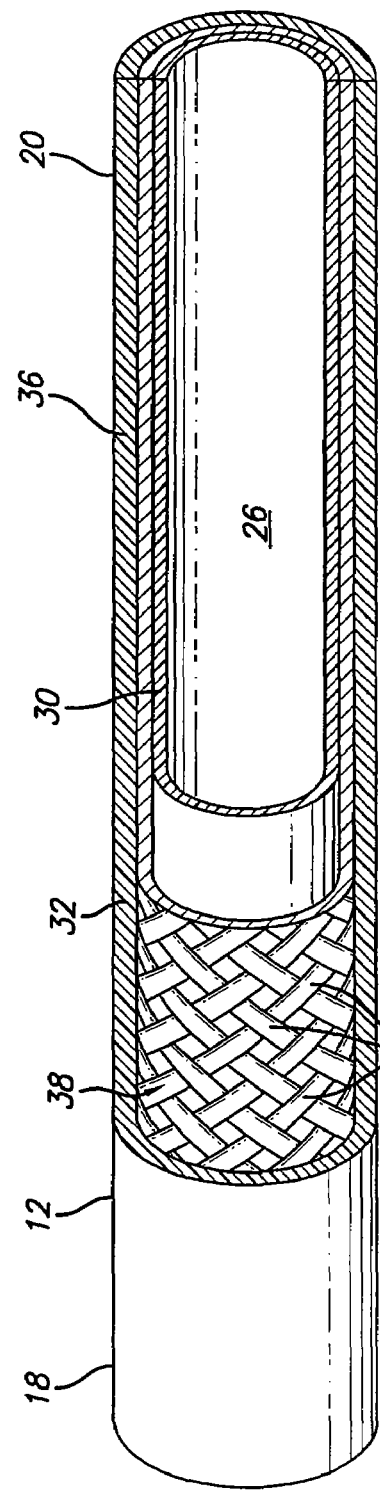
FIG. 3 is a partial cutaway perspective view of the elongated shaft of the catheter shown in FIG. 1 having a reinforcing layer formed of round wires.

In another embodiment as shown in FIG. 3, the multiple strands 40 are round drawn filled tube wires, and are braided, however, the drawn filled tube wires can also be wound around the inner layer 30. A cross-sectional view of the round drawn filled tube wires is shown in FIG. 3A, which shows the outer jacket 42 clad over the inner core 44. Using a drawn filled tube as described to form the reinforcing structure provides the guiding catheter with equivalent torque, stiffness, and enhanced radiopacity under fluoroscopy versus using a stainless steel braided wire.

It is also possible to reverse the materials used in the drawn filled tube, meaning that the outer jacket 42 of the drawn filled tube may include a radiopaque material and the inner core 44 may include stainless steel or other material with similar characteristics. A sufficient number of the drawn filled tube strands are provided to reach the desired radiopacity of the guiding catheter.

In yet another embodiment, the reinforcing structure 38 may be formed by braiding or winding together multiple spools of wires consisting of different radiopaque alloys having equivalent stainless steel properties to provide adequate torque and stiffness. It is contemplated that the reinforcing structure in this embodiment could also include strands of wires formed of stainless steel. Most of the strands forming the braided reinforcing structure are formed of a high strength, highly radiopaque metal. A substantial portion of the strands can be formed of a variety of other materials that include stainless steel (304), and high strength alloys such as MP35N, Elgiloy, Conichrome, Haynes 242 and L-605 which contain cobalt, chromium and nickel as well as high strength polymeric materials. High strength plastic strands (e.g., Kevlar) or mixtures of plastic and metallic strands may also be used to form part of the multistrand reinforcing structure. In this embodiment, at least two of the spools used to form the reinforcing structure are of different materials. As a result of using different spools of wire, the sum of the radiopaque alloys used to form the reinforcing layer will determine the amount of radiopacity detected under fluoroscopy.

In all of the mentioned embodiments for the radiopaque reinforcing layer, the combination of the number of picks, pitches and wire geometry, such as flat or round, will enhance the visualization of the guiding catheter shaft under fluoroscopy while preserving the torque and stiffness properties. These embodiments will also allow the inner diameter of the catheter to be larger while preserving the outer diameter of the catheter, and will prevent the outer layer from cracking or tearing during torsional movement. The reinforcing structure as described above can be used on any catheter having a wire braid to improve the radiopacity under fluoroscopy which will allow a physician to better view the catheter for navigational purposes.

The strands which are braided or wound to form the reinforcing structure may have a round (wire), elliptical, or rectangular (ribbon) or other transverse shape and their dimensions depend upon their mechanical properties and the desired stiffness and radiopacity. Wire diameters of about 0.0005 to about 0.003 inch (0.013-0.076 mm) are suitable. For ribbons, the short transverse cross sectional dimensions are about 0.0005 to about 0.002 inch (0.013-0.076 mm) and the long transverse direction of about 0.003 to about 0.01 inch (0.076-0.25 mm). The maximum wall thickness of the braided reinforcing structure will be located at the cross points of the strands. The transverse and longitudinal dimensions of the catheter, the materials of construction, the number, size, and spacing of the reinforcing strands will vary depending upon the end use of the catheter.

The strands which make up the reinforcing structure may be secured together to form the multistrand reinforcement into a stiffer structure. A plurality of the cross points or all of the cross points, where the individual strands cross, may be secured together by brazing, soldering, welding, suitable mechanical connections and the like to form the stiffer structure.

Guiding catheters designed for coronary artery access have varying lengths, generally between about 90 to about 130 cm, in one embodiment the length is about 100 to about 120 cm. The wall thickness of the catheter shaft ranges from about 0.003 to about 0.01 inch (0.076-0.254 mm). The thickness of the outer polymeric layer is about 0.0005 to about 0.008 inch (0.013-0.205 mm), in one embodiment the thickness is about 0.001 to about 0.003 inch (0.025-0.076 mm). The inner polymeric layer thickness is about 0.0005 to about 0.002 inch (0.013-0.051 mm), preferably about 0.0007 to about 0.0012 inch (0.018-0.031 mm). The guiding catheter has a generally constant inner and outer diameter throughout its length, and the wall thickness is also generally constant.

It will be apparent from the foregoing that, while particular forms of the invention have been illustrated and described, various modifications can be made without departing from the spirit and scope of the invention. Moreover, those skilled in the art will recognize that features shown in one embodiment of the invention may be utilized in other embodiments of the invention. To the extent not otherwise described herein, the materials and methods of construction and the dimensions of conventional intravascular guide wires may be employed with the guiding member embodying features of the present invention. While the description of the invention is directed to embodiments for coronary applications, various modifications and improvements can be made to the invention without departing therefrom. Additionally, reference to the terms "members," "elements," "sections" and terms of similar import in the claims which follow shall not be interpreted to invoke the provisions of 35 U.S.C. §112 paragraph 6 unless reference is expressly made to the term "means" followed by an intended function.

What is claimed is:

1. A guiding catheter for accessing a body lumen, comprising:
    an elongated shaft having a proximal end, a distal end and an inner lumen, the shaft including:
        an inner layer,
        an outer layer, and
        a reinforcing structure extending between the inner and outer layers, the reinforcing structure made from a plurality of radiopaque wires which are braided together, each wire having an outer jacket clad over an inner core.

2. The guiding catheter of claim 1, wherein each of the wires is flat.

3. The guiding catheter of claim 1, wherein each of the wires is a round.

4. The guiding catheter of claim 1, wherein each of the inner cores of the wires includes stainless steel, and each of the outer jackets includes a radiopaque material.

5. The guiding catheter of claim 1, wherein each of the inner cores of the wires includes a radiopaque material, and each of the outer jackets is made from stainless steel.

6. The guiding catheter of claim 5, wherein the radiopaque material of each inner core is about 5% to about 25% by cross-sectional area of each wire.

7. The guiding catheter of claim 5, wherein the radiopaque material of each inner core includes an element selected from the group consisting of platinum, gold, silver, and tantalum.

8. The guiding catheter of claim 1, wherein the wires are secured together at a plurality of cross points.

9. The guiding catheter of claim 1, wherein each of the wires is made from a drawn filled tube.

* * * * *